United States Patent
Boga et al.

(10) Patent No.: US 7,592,020 B2
(45) Date of Patent: Sep. 22, 2009

(54) PERSONAL CARE PRODUCTS WITH VISUAL INDICATOR OF VAGINITIS

(75) Inventors: RameshBabu Boga, Roswell, GA (US); John Gavin MacDonald, Decatur, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 873 days.

(21) Appl. No.: 10/961,676

(22) Filed: Oct. 8, 2004

(65) Prior Publication Data

US 2005/0124072 A1  Jun. 9, 2005

Related U.S. Application Data

(63) Continuation-in-part of application No. 10/729,811, filed on Dec. 5, 2003, now abandoned.

(51) Int. Cl.
*A61F 13/00* (2006.01)
*A61K 9/70* (2006.01)

(52) U.S. Cl. .................. 424/443; 424/400; 424/430; 424/445

(58) Field of Classification Search .............. 424/400, 424/422, 430, 431, 443, 444, 445, 446, 447, 424/448
See application file for complete search history.

(56) References Cited

U.S. PATENT DOCUMENTS

| | | |
|---|---|---|
| 2,593,146 A | 4/1952 | Howard |
| 3,004,895 A | 10/1961 | Schwartz |
| 3,266,973 A | 8/1966 | Crowley |
| 3,520,302 A | 7/1970 | Jones |
| 3,683,912 A | 8/1972 | Olson et al. |
| 4,100,324 A | 7/1978 | Anderson et al. |
| 4,375,448 A | 3/1983 | Appel et al. |
| 4,494,278 A | 1/1985 | Kroyer et al. |
| 4,511,488 A | 4/1985 | Matta |
| 4,525,410 A | 6/1985 | Hagiwara et al. |
| 4,640,810 A | 2/1987 | Laursen et al. |
| 4,775,582 A | 10/1988 | Abba et al. |
| 4,775,585 A | 10/1988 | Hagiwara et al. |
| 4,783,220 A | 11/1988 | Gamble et al. |
| 4,818,464 A | 4/1989 | Lau |
| 4,833,003 A | 5/1989 | Win et al. |
| 4,853,281 A | 8/1989 | Win et al. |
| 4,938,753 A | 7/1990 | Van Gompel et al. |
| 4,940,464 A | 7/1990 | Van Gompel et al. |
| 5,122,418 A | 6/1992 | Nakane et al. |
| 5,145,518 A | 9/1992 | Winnik et al. |
| 5,217,444 A | 6/1993 | Schoenfeld |
| 5,407,442 A | 4/1995 | Karapasha |
| 5,429,628 A | 7/1995 | Trinh et al. |
| 5,486,356 A | 1/1996 | Yim |
| 5,527,171 A | 6/1996 | Soerensen |
| 5,540,916 A | 7/1996 | Parks |
| 5,679,138 A | 10/1997 | Bishop et al. |
| 5,679,724 A | 10/1997 | Sacripante et al. |
| 5,733,272 A | 3/1998 | Brunner et al. |
| 5,817,300 A | 10/1998 | Cook et al. |
| 5,861,144 A | 1/1999 | Peterson et al. |
| 5,874,067 A | 2/1999 | Lucas et al. |
| 5,948,398 A | 9/1999 | Hanamoto et al. |
| 6,024,786 A | 2/2000 | Gore |
| 6,060,410 A | 5/2000 | Gillberg-LaForce et al. |
| 6,096,299 A | 8/2000 | Guarracino et al. |
| 6,225,524 B1 | 5/2001 | Guarracino et al. |
| 6,240,569 B1 | 6/2001 | Van Gompel et al. |
| 6,277,772 B1 | 8/2001 | Gancet et al. |
| 6,344,218 B1 | 2/2002 | Dodd et al. |
| 6,367,089 B2 | 4/2002 | Van Gompel et al. |
| 6,376,741 B1 | 4/2002 | Guarracino et al. |
| 6,460,989 B1 | 10/2002 | Yano et al. |
| 6,475,601 B1 | 11/2002 | Sakaki et al. |
| 6,491,790 B1 | 12/2002 | Proverb et al. |
| 6,517,199 B1 | 2/2003 | Tomioka et al. |
| 6,536,890 B1 | 3/2003 | Kato et al. |
| 6,576,575 B1 | 6/2003 | Griesbach, III et al. |
| 2002/0106466 A1 | 8/2002 | Hausmann et al. |
| 2002/0142937 A1 | 10/2002 | Carter et al. |
| 2003/0070782 A1 | 4/2003 | Proverb et al. |
| 2005/0084977 A1 | 4/2005 | Boga et al. |

FOREIGN PATENT DOCUMENTS

| | | |
|---|---|---|
| EP | 1216675 A1 | 6/2002 |
| WO | WO 98/07027 | 2/1998 |
| WO | WO 00/76558 | 12/2000 |

OTHER PUBLICATIONS

Cost, F., *Pocket Guide to Digital Printing*, Delmar Publishers, Albany, NY, ISBN 0-8273-7592-1, pp. 144-145.

*Primary Examiner*—D L Jones
(74) *Attorney, Agent, or Firm*—James B. Robinson; Vincent T. Kung (57) ABSTRACT

There is provided a personal care product having a body side liner, a baffle and an indicator strip with two ends. The indicator has an amine sensitive dye near at least one end. The indicator extends from the target area just below the liner to just above the baffle such that the dye deposit is visible to an unaided eye. The dye changes color in the presence of amines which are characteristic of infection, thus alerting the user to the possibility of infection. Such an indicator placed in a feminine hygiene pad, for example, may be useful in the diagnosis of vaginitis.

10 Claims, 7 Drawing Sheets

PERSONAL CARE PRODUCTS WITH VISUAL INDICATOR OF VAGINITIS

This application is a Continuation-In-Part of U.S. patent application Ser. No. 10/729,811 filed Dec. 5, 2003, now abandoned commonly assigned, and claims priority from that case.

BACKGROUND OF THE INVENTION

The invention concerns processes and products for the indication of infection such as in vaginitis.

Vaginal infections are the most common women's health problem, and commonly or medically referred to as vaginitis. Vaginal infections are the most frequent reason American women see their doctors, and account for more than 1.0 million office visits per year. Vaginal infection ("vaginitis"), for example, exists in three primary forms, i.e., bacterial vaginosis, candidal vaginitis ("yeast"), and trichomonas vaginitis ("trich"). The most prevalent type of infection is bacterial vaginosis, affecting up to 40 to 50% of American women of childbearing age.

Evidence suggests that pregnant women diagnosed with bacterial vaginosis have an elevated risk for preterm labor or premature rupture of the amniotic membrane, putting both mother and baby at higher risk. Additional possible adverse outcomes include an increased frequency of abnormal papanicolaou (Pap) smears, pelvic inflammatory disease and endometritis.

The most characteristic symptoms of vaginal infection are discharge, odor, irritation, and elevation of pH and amine(s) level. Various mono- and di-amines are produced by anaerobic bacteria, and result in odor in the vaginal fluid with bacterial vaginosis.

Various techniques have been developed in an attempt to rapidly diagnose the forms of vaginitis. For example, microbiological techniques have been utilized to identify "clue cells" (vaginal epithelial cells with adherent surface bacteria). Conventional techniques for confirming the presence of "clue cells", however, are often complicated and slow. Likewise, techniques have been utilized that detect an elevated pH level in an infected sample. Unfortunately, conventional techniques for detecting an elevated pH level are often misleading due to other factors, such as the use of antimicrobials and cervical discharge, which also cause an elevated pH. Several detection methods are known for amines, these methods, however, have complex multiple steps, require expensive instrumentation, or are time-consuming.

It is clear that there exists a need for a process and product which allows for the rapid, inexpensive, and non-invasive detection of vaginitis infections.

SUMMARY OF THE INVENTION

In response to the foregoing difficulties encountered by those of skill in the art, we have developed a personal care product having a visual indicator for the presence of amines generated by microbes, thus signaling the possible presence of infection. The typical personal care product has a body side liner and a baffle and may have an absorbent pad there between. An indicator strip may be placed in the product. The indicator has an amine sensitive dye deposit that may be near at least one end. The indicator may be in the target area only or may extend from the target area and/or the middle of pad. The indicator may extend from just below the liner to just above the baffle such that the dye deposit is visible to an unaided eye either from the liner side. (body) or baffle side (garment). The dye changes color in the presence of amines which are characteristic of infection, thus alerting the user to the possibility of infection. A feminine hygiene pad having such an indicator, for example, may be useful in the diagnosis of vaginitis. Similarly, the indicator is useful in diagnosing vaginitis by placing it into tampons, swabs, removable patches, reusable underwear, and the like.

Also disclosed is a method of providing a system for visually indicating the presence of amines that are characteristic of vaginitis, the method. The method includes the steps of providing a feminine hygiene pad having an indicator, providing instructions to enable a user to properly place the pad, providing instructions to enable a user to visually examine the indicator at an appropriate time, providing instructions to enable a user to visually interpret changes in the indicator, so that a user is enabled to utilize the system to visually indicate the presence of amines that are characteristic of vaginitis.

BRIEF DESCRIPTION OF THE DRAWINGS

FIG. 5 has plan (a) and cross-sectional (b) views of a feminine hygiene pad having an indicator strip wherein only one end of the strip has dye.

FIG. 6 has plan (a) and cross-sectional (b) views of a feminine hygiene pad having an indicator strip wherein both ends of the strip have dye.

FIG. 7 is a plan (a) and cross-sectional (b) view of a feminine hygiene pad having an indicator in the middle of the pad liner.

DETAILED DESCRIPTION OF THE INVENTION

The present invention involves the visual indication of infection in vaginitis. Such an indicator may be placed in personal care products, e.g.; absorbent underpants and feminine hygiene products.

Bacterial vaginosis (BV) is the most common vaginal infection. Bacterial vaginosis (BV) affects up to 40 to 50% of American women of childbearing age, and is caused by increased anaerobic bacteria in the vagina that leads to characteristic amine production and odor. Various amines are produced by anaerobic bacteria, and these amines are released into the vaginal fluid in bacterial vaginosis (BV).

In addition to BV, trichomonas is a common sexually transmitted disease (STD) that affects 2 to 3 million Americans yearly. It is caused by a single-celled protozoan parasite called *trichomonas vaginalis*. Trichomoniasis is primarily an infection of the urogenital tract; the urethra is the most common site of infection in men, and the vagina is the most common site of infection in women. Though trichomoniasis occurs in men, they have no symptoms, whereas in women symptoms usually appear within four to 20 days of exposure. One of the diagnostic criteria for trichomonas is the detection of a fishy amine odor.

Vaginal yeast infection or vulvovaginal candidiasis is the second most common cause of vaginitis in the US and the most common cause in Europe.

Doctors estimate that approximately 75 percent of all women will experience at least one symptomatic yeast infection during their lifetimes, and approximately 5 percent of women will have recurrent episodes. *Candida albicans* is the infecting agent in 80 to 90 percent of the yeast infected patients, and the doctor usually diagnoses yeast infection through microscopic examination of vaginal secretions for evidence of yeast forms such as *candida albicans*. Both pH and amine odors are not significantly changed in yeast vaginitis compared to normal women.

Both bacterial vaginosis and trichomoniasis produce telltale amine odors. In bacterial vaginosis, several members of anaerobic bacteria, prevotella, bacteroides, mobiluncus, and peptococcus, are present in large numbers in the vagina. Some of these organisms produce metabolic products such as amines, including trimethyl amine, putrescine, cadaverine, and tyramine which are is responsible for the odor noticed by the affected patients. A "Whiff test" is routinely conducted for amine odors where enhanced odor is generated by adding strong alkali to the sample, however, this test must be professionally performed and the use of strong alkali is not applicable to personal care products due to the caustic nature of the chemical.

Other diagnosis factors such as pH and microscopic observation of clue cells (Coccobacilli) are indicative for bacterial vaginosis. "Clue cells" are observed in 90% of patients with bacterial vaginosis. Though elevated pH (at around 4.5 or greater) supports a diagnosis of bacterial vaginosis or trichomoniasis, certain other factors such as the use of antimicrobials and cervical discharge could be a misleading cause of the elevated pH. The normal vaginal environment is characterized by a dynamic interrelationship between *Lactobacillus acidophilus* and other endogenous flora, estrogen, glycogen, vaginal pH and the metabolic by-products of flora and pathogens. *Lactobacillus acidophilus* produces hydrogen peroxide, which is toxic to pathogens and keeps the healthy vaginal pH between 3.8 and 4.2.

The inventors have discovered that an amine sensitive chemichromic dye can be used to indicate the presence of amines in vaginal odor and thus to signal a possible infection. After an extensive search for amine-sensitive dyes, three dyes with different color spectrum were identified for the indication of amine odors, though others with similar characteristics regarding their reaction to amines may also be used. One class of chemichromic dyes that is particularly useful is arylmethane dyes, such as diarylmethanes, triarylmethanes, and the like.

Triarylmethane dyes, for example, may have the following general structure:

wherein R, R', and R" are independently selected from substituted and unsubstituted aryl groups, such as phenyl, naphthyl, anthracenyl, etc. The aryl groups may, for example, be substituted with functional groups, such as amino, hydroxyl, carbonyl, carboxyl, sulfonic, alkyl, and/or other known functional groups. When contacted with the dye, the amino group of the amine (e.g., ammonia, diamines, and/or tertiary amines) reacts with the central carbon atom of the dye. The addition of the amino group causes the dye to undergo a change in color. An example of the resulting structure is set forth below:

One particular example of a suitable triarylmethane dye is pararosanilin (also known as "basic fuchsin" or "magenta 0") and analogs thereof, such as rosanilin ("magenta I"), magenta II, new fuchsin ("magenta III"), methyl violet 2B, methyl violet 6B, methyl violet 10B ("crystal violet"), methyl green, ethyl green, acid fuchsin, and so forth. Pararosanilin shifts from a red color to colorless (i.e., white) upon reaction with an amine. Pararosanilin contains three phenylamine groups (i.e., amino-substituted aryl groups). Specifically, the structure of the structure of pararosanilin is set forth below:

In some cases, triarylmethane dyes may be formed by converting a leuco base to a colorless carbinol and then treating the carbinol with an acid to oxidize the carbinol and form the dye. Thus, for example, pararosanilin may be derived by reacting the carbinol form of pararosanilin ("pararosaniline base") with an acid, such as, but not limited to, sulfonic acids, phosphoric acids, hydrochloric acid, and so forth. The carbinol form of pararosanilin is set forth below.

Another example of a suitable triarylmethane dye is alpha-naphtholbenzein and analogs thereof. Alpha-naphtholbenzein turns from an orange/red color to a gray/black color upon reaction with an amine. Alpha-naphtholbenzein contains a hydroxyl-substituted naphthyl group, a carbonyl-substituted naphthyl group, and a phenyl group. Specifically, the structure of alpha-naphtholbenzein is set forth below:

Still another example of a suitable triarylmethane dye is naphthocrome green and analogs thereof. Naphthocrome green turns from a pale yellow color to a blue/green color upon reaction with an amine. Similar to alpha-naphtholbenzein, naphthocrome green contains a hydroxyl-substituted naphthyl group, a carbonyl-substituted naphthyl group, and a phenyl group. However, each naphthyl group is also substituted with a sodium carboxyl. Specifically, the structure of naphthocrome green is set forth below:

As indicated above, diarylmethanes may also be used. One example of such a diarylmethane is 4,4'-bis(dimethylamino) benzhydrol (also known as "Michler's hydrol"), which has the following structure:

Still other examples include analogs of Michler's hydrol, such as Michler's hydrol leucobenzotriazole, Michler's hydrol leucomorpholine, Michler's hydrol leucobenzenesulfonamide, and so forth, as well as other diarylmethanes, such as malachite green leuco, malachite green carbinol, sodium 2,6-dichloroindopheno-late, rhodamine lactam, crystal violet lactone, and crystal violet leuco.

Three common amines present when infection occurs are trimethylamine (TMA), putrescine (1,4-diaminobutane or 1,4 DAB) and cadaverine (1,5-diamino pentane or 1,5 DAP) and all are available in laboratory quantities from the Sigma-Aldrich Chemical Company of Milwaukee, Wis., USA. A simple and rapid detection of cadaverine (1,5-DAP), Putrescine (1,4-DAB), and trimethylamine (TMA) was demonstrated by applying drops of these amines on alpha-naphtholbenzein. (ANB) coated paper. These amines rapidly changed the dye color from orange yellow to grey/black. It was also found that these amines could change the color of the dye when the amines were in the gaseous state when the dye did not come into contact with the liquid amine.

Personal care products in which the indicator may be placed include swabs, diapers and feminine hygiene products like pads, tampons and absorbent underpants. The indicator may be a removable patch. The indicator may be placed, for example, in every product in a package containing multiple products or may be placed in every second, third or fifth product in the package, etcetera.

As used herein, the term "biological sample" generally refers to a biological material suspected of containing the analyte. The biological sample may be obtained or derived from any biological source, such as a physiological fluid, including, blood, menses, interstitial fluid, saliva, ocular lens fluid, cerebral spinal fluid, sweat, urine, milk, ascites fluid, mucous, synovial fluid, peritoneal fluid, vaginal fluid, amniotic fluid, and so forth.

Figure 1:
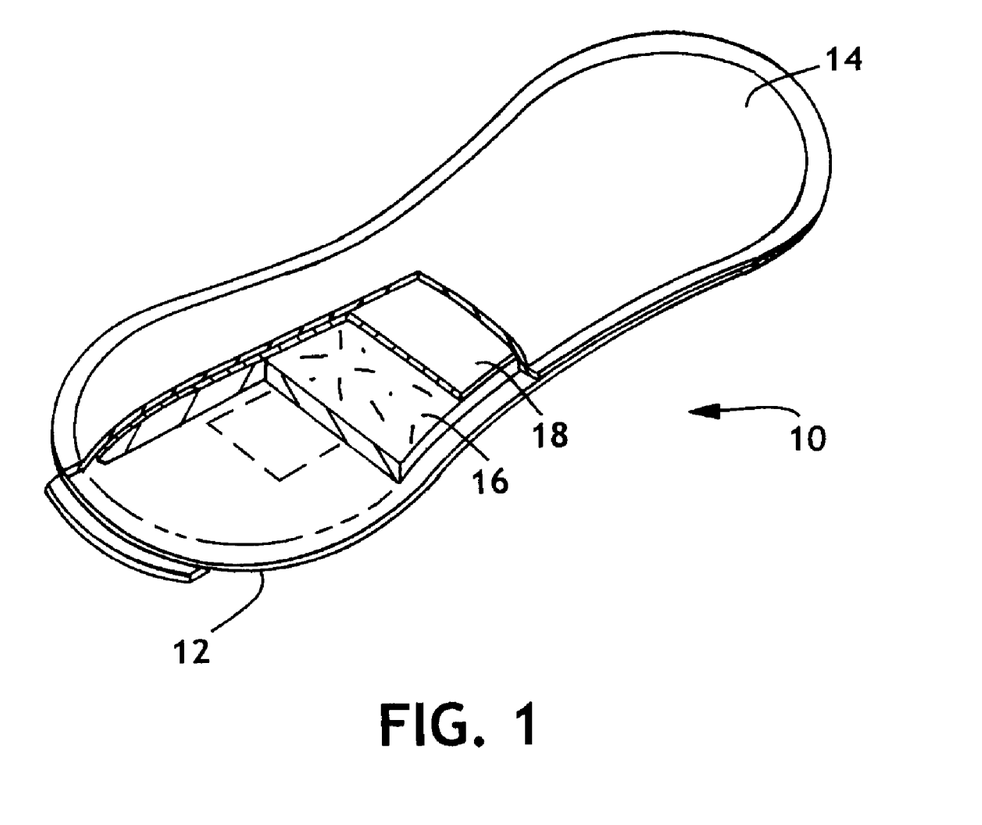
FIG. 1 is a broken away drawing of a feminine hygiene product.

Feminine hygiene products include, for example, the pad shown in FIG. 1. This pad 10 has a liquid impervious baffle 12 on the side away from the wearer. The baffle 12 is often made from a film like a polyethylene or polypropylene film and is transparent or translucent. The layer closest to the wearer is the body side liner 14 and is a liquid pervious layer that is preferably soft and absorbent. Between the baffle 12 and liner 14 there may be a number of layers for different purposes, such as an absorbent core 16 designed to hold the majority of any liquid discharge. Other optional layers include transfer delay layers 18, and tissue wraps (not shown).

Figure 2:
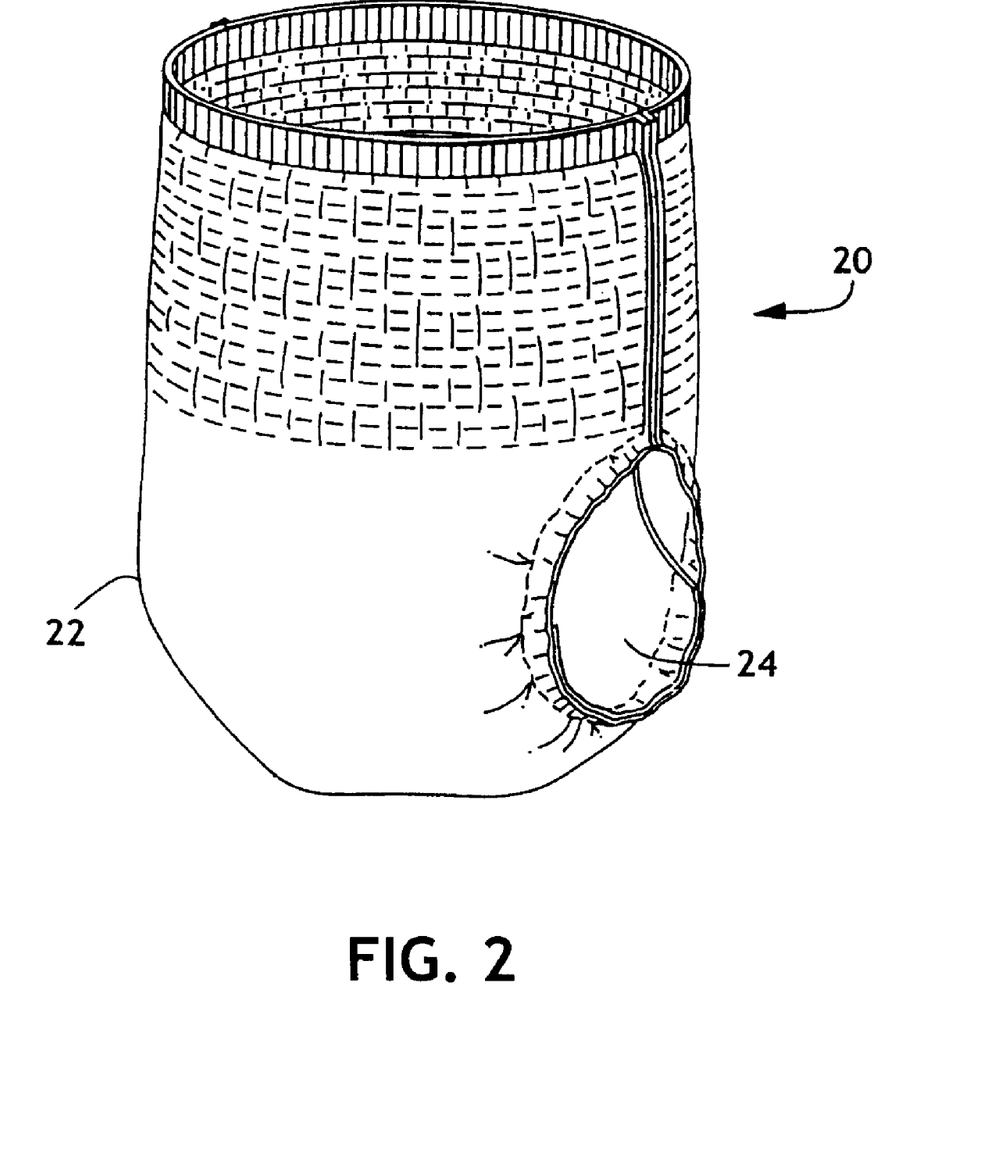
FIG. 2 is a drawing of an absorbent underpant.

Absorbent underpants 20 as shown in FIG. 2 have a baffle 22, liner 24 and absorbent core (not shown). A further discussion regarding absorbent underpants may be found, for example, in U.S. Pat. Nos. 6,240,569 and 6,367,089 which are incorporated herein in their entirety by reference thereto for all purposes.

Figure 3:
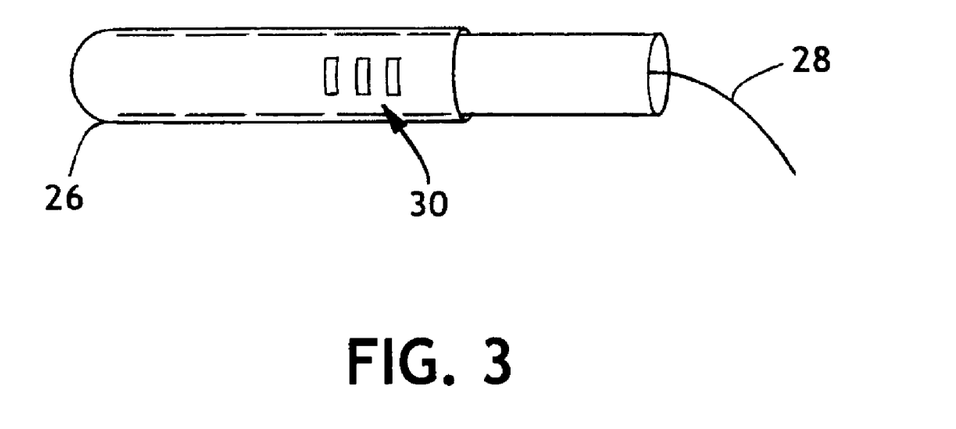
FIG. 3 is a drawing of an indicator in a tampon.

A tampon as shown in FIG. 3 may also contain the indicator 30. Tampons have the general structure as described in U.S. Pat. Nos. 3,520,302 and 3,683,912 which are incorporated herein in their entirety by reference thereto for all purposes. The generally elongate shape of a tampon typically has an absorbent body 26 and a withdrawal string 28. Additional structural features may also be present.

The indicator may be placed in a standard cotton swab so that it is visible on the end. The swab may have cotton at one or both ends. The dye portion of the indicator may be between the ends of the swab so that amines contacted by the ends of the swab will move toward the dye located in a more visible portion of the swab and thus be more easily observed by a user.

Figure 4:
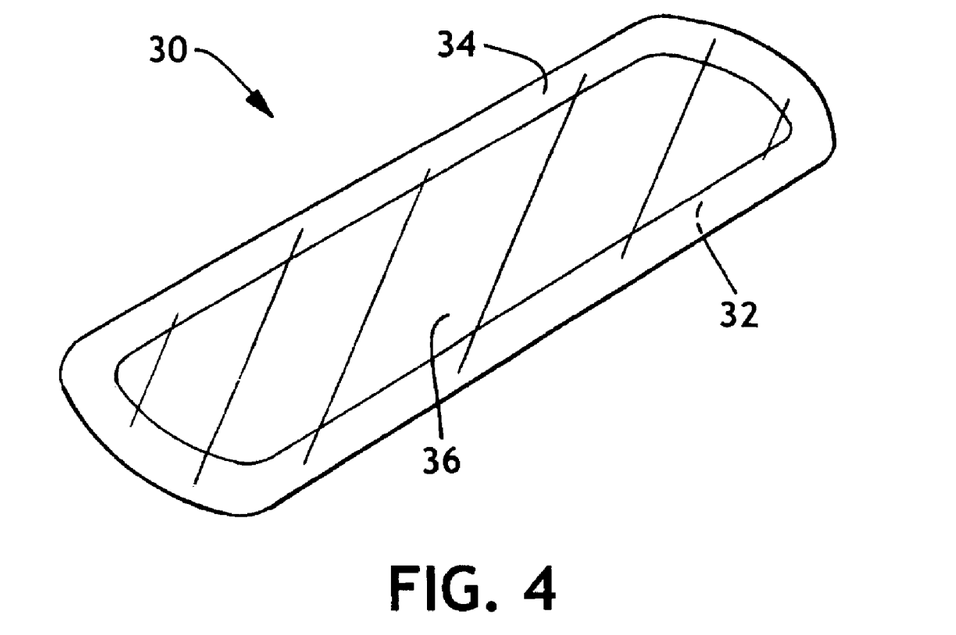
FIG. 4 is a drawing of an indicator strip.

The indicator which may be placed in the personal care products described above will now be described in greater detail with reference to FIG. 4. As shown, the indicator 30 contains a porous membrane 32 that acts as a fluidic medium. In general, the porous membrane 32 may be made from any of a variety of materials through which the test sample is capable of passing. The materials used to form the porous membrane 32 may include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the porous membrane 32 is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

The indicator 30 may also contain an absorbent pad 34. The absorbent pad 34 generally receives fluid that has migrated through the entire porous membrane 32. As is known in the art, the absorbent pad 34 may assist in promoting capillary action and fluid flow through the membrane 32.

The indicator 30 contains a detection zone 36 that may generally provide any number of distinct detection regions so that a user may better determine the concentration of a particular analyte within a test sample. Each region may contain a deposit of the chemichromic dye, or may contain different dyes for reacting with different types of amines. The detection zone 36 may, for example, include two or more distinct detection regions (e.g., lines, dots, etc.). The detection regions may be disposed in the form of lines in a direction that is substantially perpendicular to the flow of the test sample through the indicator 30. In some embodiments the detection regions may be disposed in the form of lines in a direction that is substantially parallel to the flow of fluid through the indicator 30. The size of the dye deposit in the detection zone 36 may be varied, with the sole requirement being that it be of sufficient size and quantity to be seen by the unaided eye. Dye deposits as small as a few millimeters in area to as large as necessary may be produced, with the most likely sizes for personal care products being between 0.25 $cm^2$ and 5 $cm^2$, more desirably between about 0.5 $cm^2$ and 3 $cm^2$, still more desirably between 1 $cm^2$ and 2 $cm^2$.

The indicator 30 may be of any size appropriate to the personal care product in which it is to be used. In particular, a size of between about 0.25 and 3 centimeters in width and about 8 to 25 cm in length may be used. More particularly a width of about 1 to 2 cm and length of about 10 to 15 cm may be appropriate for many feminine hygiene pad products. Still more particularly a width of about 1.3 cm and a length of about 12 cm may be appropriate.

Figure 5A:
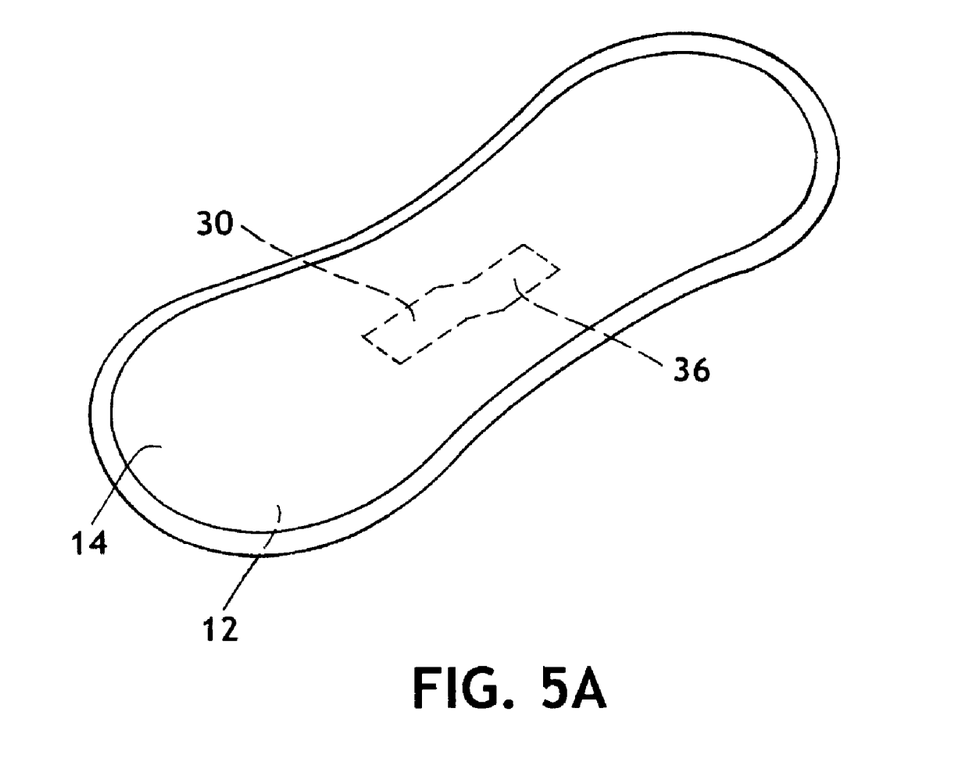
Figure 5B:
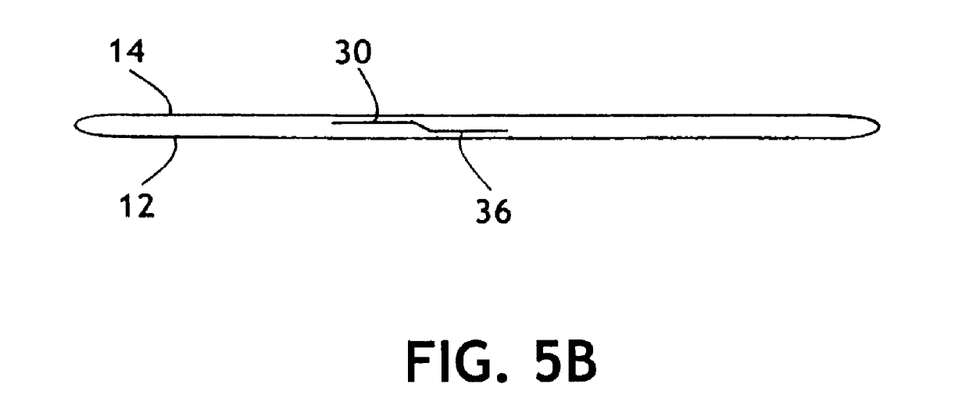

As shown in FIGS. 5a and 5b (length-wise cross-section) in one embodiment of a feminine hygiene pad, the indicator 30 may be placed below the liner 14 in one area of the pad and extend to just above the baffle 12. In this location adjacent to the liner the indicator may be contacted directly by any discharge, yet is still appropriately located so that it may be seen by the user upon removal. It should be noted that the indicator may be located in the "target area" (the area where discharges generally impact upon the product). The important factor is that it be visible to a user after amine exposure. In use, upon receipt of a discharge, the fluid will pass through the liner 14 and come in contact with the indicator 30. The fluid will travel along the indicator 30 and eventually contact the chemichromic dye(s) in the detection zone 36. This will cause a color change if there are amines present. Upon removal of the pad, the detection zone 36 will be visible through the baffle 12. A color change will alert the user to the possibility of infection and the need to seek treatment.

Figure 6A:
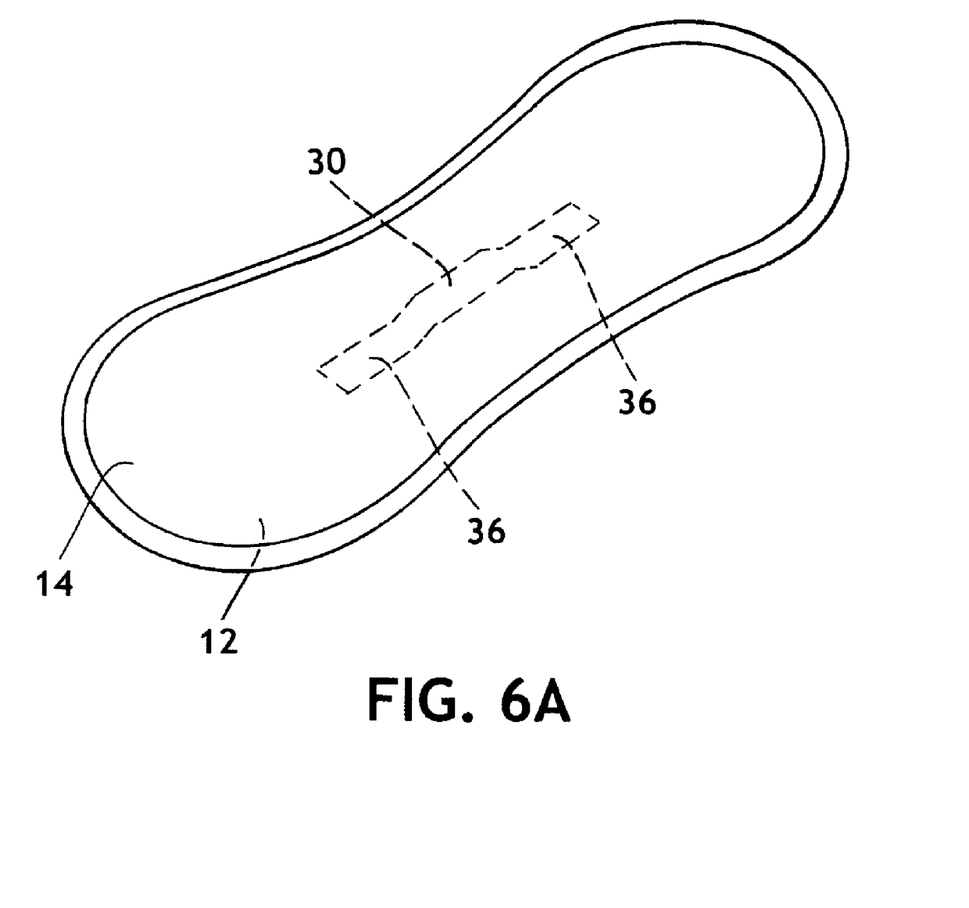
Figure 6B:
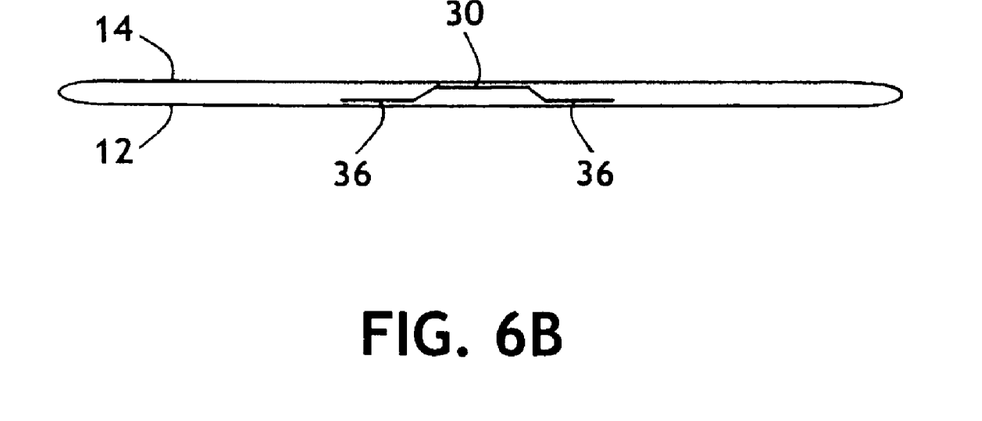

In yet another embodiment, as shown in FIGS. 6a and 6b (length-wise cross-section), the indicator 30 may be placed below the liner 14 in the target area and both ends of the indicator 30 may extend to just above the baffle 12. Again, the indicator 30 may be contacted by any discharge in the target area, which will travel along the indicator 30 to the detection zones 36 and, if amines are present, cause a color change visible to the user through the baffle 12.

Figure 7A:
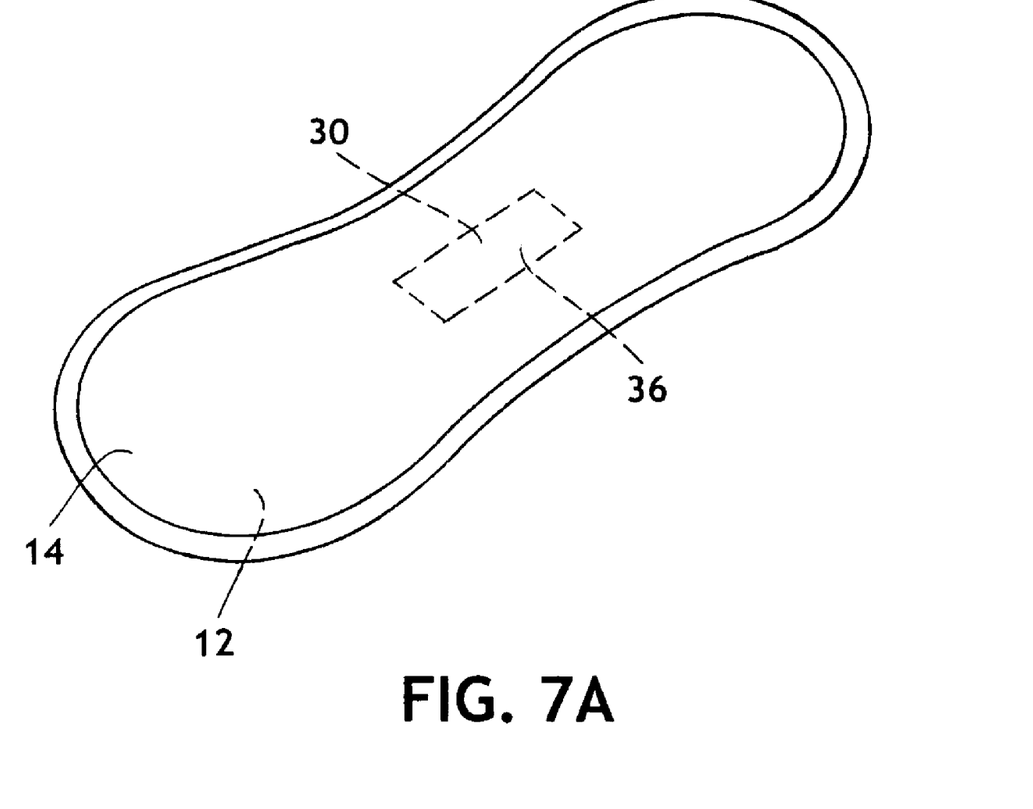
Figure 7B:
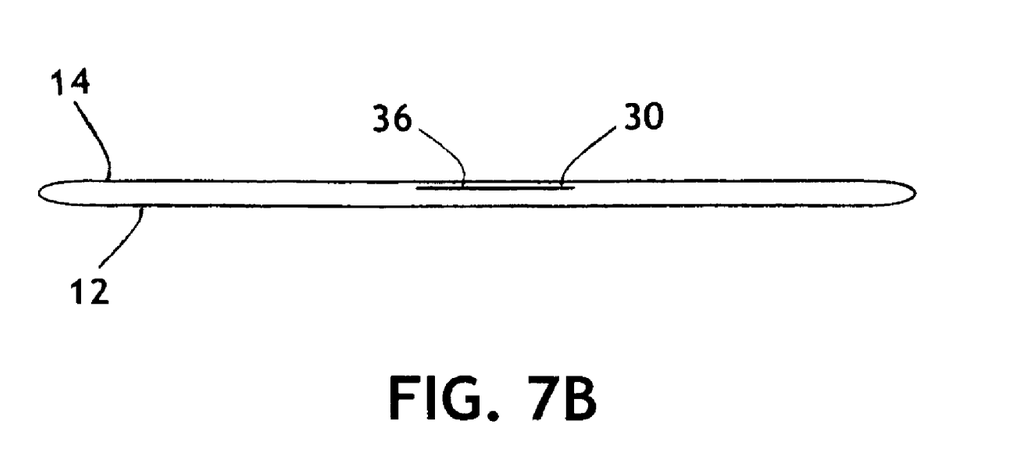

In still another embodiment as shown in FIGS. 7a and 7b (length-wise cross-section), the indicator 30 with dye in the detection zone 36 may be inserted just below the liner 14 in, for example, the target area. In this position the indicator will change color when contacted with amine containing discharges and be visible through the liner when the product is removed from the body. In this case the detection zone 36 may be the size of the entire indicator 30.

The indicator may be a removable patch that may be positioned by a user in a product such as a feminine hygiene pad. The patch may be held in place with any appropriate means such as by adhesive, hook and loop fastener, and so forth.

Figure 8:
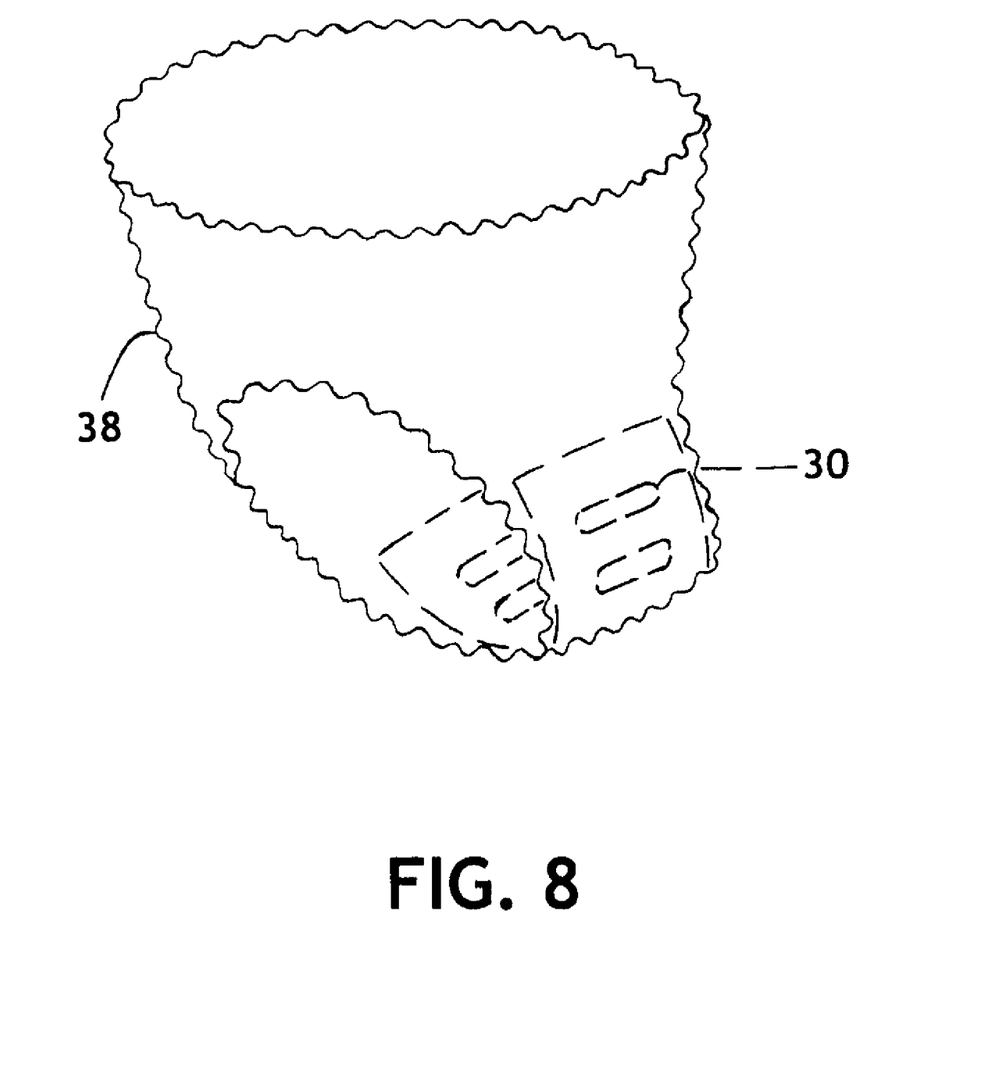
FIG. 8 is a drawing of a diaper having an indicator in the target area.

FIG. 8 shows the indicator 30 located in the target area of a diaper 38. This indicator may be of the removable patch type or may be permanently mounted in the diaper 38.

Any of a variety of techniques may be employed to apply the dye to the porous membrane 32, regardless of which dye may be chosen. The dye may be applied directly to the membrane 32 or first formed into a solution prior to application. Various solvents may be utilized to form the solution, such as, but not limited to, acetonitrile, dimethylsulfoxide (DMSO), ethyl alcohol, dimethylformamide (DMF), and other polar organic solvents. The amount of the dye in the solution may range from about 0.001 to about 10 milligram per milliliter of solvent, and in some embodiments, from about 0.01 to about 0.1 milligrams per milliliter of solvent. The dye solution may be coated onto the porous membrane 32 using known methods and then dried. The dye may be coated onto the substrate layer by the dip and squeeze method, which entails dipping the layer into a solution having the absorbent and binder, squeezing out the excess, and drying. The dye may alternatively be applied to the substrate by placing a few drops of the dye solution on the desired area and allowing the substrate to air-dry, as for example. The dye concentration may be selectively controlled to provide the desired level of detection sensitivity; for example, higher concentrations may provide a higher level of detection sensitivity when low amine levels are suspected. Printing techniques like ink jet printing, rotogravure printing and other techniques known to those skilled in the art may suitable be used to apply the dye to the substrate.

The dye may be applied, as indicated herein, in a pattern of circular dots. Many other sizes and patterns for the dye may be used, of course, including lettering such as "See your doctor" and the like. The issue is that the area of the dye in the product be visible by the unaided eye after the product is used. In this way the color change, from colored to colorless, from colorless to colored, or from one color to another color, will alert the user to the need to seek medical attention.

The following examples aid in understanding the invention.

EXAMPLE 1

A visual indicator was incorporated into a Kotex Lightdays Ultra coverage (purse-paks, unscented) feminine hygiene pad as a small strip of tissue and demonstrated to be sensitive to the amine-based vaginal odors. ANB dye at a concentration of 50-5000 micrograms was coated onto a cellulose towel substrate and allowed to air dry, producing an orange color. Small strips (1 cm×2 cm) of the towel were then inserted into the pad at one end under the body side liner. The orange colored strip was still quite visible. The pad was then insulted with 10 microliters of a 10 mg/ml TMA amine solution at a concentration of 100 micrograms placed in the target area of the pad, and then the pad was placed into a 1 quart, glass jar and sealed. The liquid amine did not directly touch the dye. The orange color of the cellulose strip rapidly changed color to a grey/black color, indicating the presence of amines and therefore serving as an alert signal for potential vaginitis.

This experiment demonstrates the potential application for the visual indicator to detect the amine odor from the center of the pad and act as visual alert to the user. It is noted that the strip did not come in contact with the odorous liquid, and the observed color change was therefore due to the gaseous odor.

EXAMPLE 2

A visual indicator was incorporated into a Kotex Lightdays Long (unscented) feminine hygiene pad as a small strip of nitrocellulosic material and demonstrated to be sensitive to the amine-based vaginal fluid. ANB dye at a concentration of 50-5000 micrograms was placed on the strip on one end in three relatively circular dots with a diameter of about 7 mm and allowed to air dry, producing an orange color. A strip (1.3 cm×8 cm) of the material was then inserted into the pad as shown in FIG. 5 with the three dots on the end just above the baffle. The dots on the strip were visible through the baffle but the strip was not visible through the body side liner. The pad was then insulted with 200 microliters of a 1.5 mg/ml mixed amine (TMA, 1,5-DAP, 1,4-DAB, and Tyramine) solution-placed in the target area of the pad. The orange color of the dye deposits changed color to a grey/black color after approximately <5 minutes, indicating the presence of amines and therefore serving as an alert signal for potential vaginitis. The dots of dye changed color sequentially with the dot closest to the target area changing color first and the others following in order.

This experiment demonstrates the potential application for the visual indicator to detect amines from the center of the pad and act as visual alert to the user.

EXAMPLE 3

A visual indicator was incorporated into a Kotex Lightdays. Long (unscented) feminine hygiene pad as a small strip of nitrocellulosic material and demonstrated to be sensitive to the amine-based vaginal fluid. ANB dye at a concentration of 50-5000 micrograms was placed on the strip on both ends in three relatively circular dots with a diameter of about 7 mm and allowed to air dry, producing an orange color. A strip (1.3 cm×8 cm) of the material was then inserted into the pad as shown in FIG. 5 with the three dots on each end just above the baffle. The dots on the strip were visible through the baffle but the strip was not visible through the body side liner. The pad was then insulted with 200 microliters of a 1.5 mg/ml mixed amine (TMA, 1,5-DAP, 1,4-DAB) solution placed in the target area of the pad. The orange color of the dye deposits changed color to a grey/black color after approximately <5 minutes, indicating the presence of amines and therefore serving as an alert signal for potential vaginitis. The dots of dye changed color sequentially with the dot closest to the target area changing color first and the others following in order.

EXAMPLE 4

A visual indicator was incorporated into a Kotex Lightdays Long (unscented) feminine hygiene pad as a small strip of nitrocellulosic material and demonstrated to be sensitive to the amine-based vaginal fluid. ANB dye at a concentration of 50-5000 micrograms was placed on the strip on both ends in three relatively circular dots with a diameter of about 7 mm and allowed to air dry, producing an orange color. A strip (1.3 cm×8 cm) of the material having the three dots on each end was then inserted into the pad with the ends just above the baffle as shown in FIG. 6. The dots on the strip were visible through the baffle but the strip was not visible through the body side liner. The pad was then insulted with 200 microliters of normal vaginal secretion sample placed in the target area of the pad, and the solution was flowed from the center zone to the indicator zone by <10 minutes.

EXAMPLE 5

A visual indicator was incorporated into a Kotex Lightdays Long (unscented) feminine hygiene pad as a small strip of nitrocellulosic material and demonstrated to be sensitive to the amine-based vaginal fluid. ANB dye at a concentration of 50-5000 micrograms was placed on the strip on both ends in three relatively circular dots with a diameter of about 7 mm and allowed to air dry, producing an orange color. A strip (1.3 cm×8 cm) of the material having the three dots on each end was then inserted into the pad with the ends just above the baffle as shown in FIG. 6. The dots on the strip were visible through the baffle but the strip was not visible through the body side liner. The pad was then insulted with 200 microliters of vaginal secretion sample with spiked amines (1.5 mg/ml concentration of mixed amines TMA, 1,5-DAP, 1,4-DAB, and tyramine) placed in the target area of the pad. The orange color of the dye deposits changed color to a grey/black color after approximately <10 minutes, indicating the presence of amines and therefore serving as an alert signal for potential vaginitis. The dots of dye changed color sequentially with the dot closest to the target area changing color first and the others following in order.

EXAMPLE 6

A visual indicator was incorporated into a Kotex Lightdays Long (unscented) feminine hygiene pad as a small strip of nitrocellulosic material and demonstrated to be sensitive to the amine-based vaginal fluid. ANB dye at a concentration of 50-5000 micrograms was placed on the strip on both ends in three relatively circular dots with a diameter of about 7 mm and allowed to air dry, producing an orange color. A strip (1.3 cm×8 cm) of the material having the three dots on each end was then inserted into the pad with the ends just above the baffle as shown in FIG. 6. The dots on the strip were visible through the baffle but the strip was not visible through the body side liner. The pad was then insulted with 200 microliters of normal menses sample placed in the target area of the pad, and the solution was flowed from the center zone to the indicator zone by <5 minutes.

EXAMPLE 7

A visual indicator was incorporated into a Kotex Lightdays Long (unscented) feminine hygiene pad as a small strip of nitrocellulosic material and demonstrated to be sensitive to the amine-based vaginal fluid. ANB dye at a concentration of 50-5000 micrograms was placed on the strip on both ends in three relatively circular dots with a diameter of about 7 mm and allowed to air dry, producing an orange color. A strip (1.3 cm×8 cm) of the material having the three dots on each end was then inserted into the pad with the ends just above the baffle as shown in FIG. 6. The dots on the strip were visible through the baffle but the strip was not visible through the body side liner. The pad was then insulted with 200 microliters of menses sample with spiked amines (1.5 mg/ml concentration of mixed amines TMA, 1,5-DAP, 1,4-DAB, and tyramine) placed in the target area of the pad. The orange color of the dye deposits changed color to a grey/black color after approximately <10 minutes, indicating the presence of amines and therefore serving as an alert signal for potential vaginitis. The dots of dye changed color sequentially with the dot closest to the target area changing color first and the others following in order.

EXAMPLE 8

Assay devices were prepared from a nitrocellulose porous membrane (HF 12002 from Millipore, Inc.) having a length of approximately 30 centimeters laminated onto a corresponding supporting card (60 mm×301 mm from Millipore Corporation part number HF00MC100). Chemichromic detection zones were formed on each of the devices using a stock solution (~8.0 milligrams per milliliter) of alpha-naphthol-benzein (Sigma-Aldrich Chemical Company) in a methanol/water mixture (4/6 ratio). One (1) microliter of this stock solution was then spotted onto the assay devices to form the circular indicator zone, and the devices were then dried for 30 minutes at room temperature (25° C.). A cotton swab dipped normal vaginal sample was applied onto circular indicator zone to produce a color change from orange to grey/black color.

EXAMPLE 9

Assay devices as described above in Example 8 were used with a vaginal sample with additional "spiked" amines (1.5 mg/ml concentration of mixed amines TMA, 1,5-DAP, 1,4-DAB, and tyramine) and a cotton swab dipped in this solution was placed onto the circular indicator zone to produce a color change. The orange color of the indicator zone changed color to a grey/black color after 1-2 minutes, indicating the presence of amines and therefore serving as an alert signal for potential vaginitis.

EXAMPLE 10

Assay devices as described above in Example 8 were used for menstrual samples and cotton swabs dipped in the samples were placed onto the circular indicator zones to produce a color change.

EXAMPLE 11

Assay devices as described above in Example 8 were used for menstrual samples spiked with amines (1.5 mg/ml concentration of mixed amines TMA, 1,5-DAP, 1,4-DAB, and tyramine) and a dipped cotton swab was placed onto the circular indicator zones to produce a color change. The orange color of the indicator zone changed color to a grey/black color after 1-2 minutes, indicating the presence of amines and therefore serving as an alert signal for potential vaginitis. This experiment demonstrates the potential application for the visual indicator to detect amines from the center of the pad and act as visual alert to the user.

As will be appreciated by those skilled in the art, changes and variations to the invention are considered to be within the ability of those skilled in the art. Examples of such changes are contained in the patents identified above, each of which is incorporated herein by reference in its entirety to the extent it is consistent with this specification. Such changes and variations are intended by the inventors to be within the scope of the invention. It is also to be understood that the scope of the present invention is not to be interpreted as limited to the specific embodiments disclosed herein, but only in accordance with the appended claims when read in light of the foregoing disclosure.

What is claimed is:

1. A feminine hygiene pad comprising: a liquid impervious baffle, a liquid pervious body side liner, a targeting area, and an indicator strip having applied thereto an amine sensitive dye selected from the group consisting of pararosaniline base (PAB), alpha-naphthol-benzein (ANB), and naphthochrome green (NCG) and mixtures thereof.

2. The feminine hygiene pad according to claim 1, wherein said dye is present in an amount of between about 0.0001 and 20 weight percent on a dry basis.

3. The feminine hygiene pad according to claim 1, wherein said indicator strip is selected from the group consisting of: cellulose, woven or nonwoven fabric, cotton, silk, rayon, glass fiber, films, silica gels and latex particles.

4. The feminine hygiene pad according to claim 1 wherein said indicator scrip is between about 0.25 and 3 centimeters in width and about 8 to 25 cm in length.

5. The feminine hygiene pad according to claim 4, wherein said indicator strip is between about 1 to 2 cm in width and about 10 to 15 cm in length.

6. The feminine hygiene pad according to claim 1, wherein said amine sensitive dye is placed such that said dye is visible to an unaided eye.

7. The feminine hygiene pad according to claim 1, wherein said amine sensitive dye is placed in sequential dots proximal to least one end of said indicator strip.

8. The feminine hygiene pad according to claim 1, wherein said indicator strip extends from immediately below said liner in said target area to immediately above said baffle.

9. The feminine hygiene pad according to claim 1, wherein only one end of said indicator strip is placed adjacent to said baffle.

10. The feminine hygiene pad according to claim 1, wherein said indicator strip has two ends and both ends of are placed adjacent to said baffle.

* * * * *

UNITED STATES PATENT AND TRADEMARK OFFICE
CERTIFICATE OF CORRECTION

PATENT NO. : 7,592,020 B2  
APPLICATION NO. : 10/961676  
DATED : September 22, 2009  
INVENTOR(S) : Boga et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1323 days.

Signed and Sealed this

Fourteenth Day of December, 2010

David J. Kappos  
*Director of the United States Patent and Trademark Office*